United States Patent [19]
Cathel et al.

[11] Patent Number: 5,342,497
[45] Date of Patent: * Aug. 30, 1994

[54] ELECTROPHORESIS SYSTEM

[75] Inventors: Frank Cathel, Descanso; Robert Leshofs, San Diego, both of Calif.

[73] Assignee: Stratagene Cloning Systems, La Jolla, Calif.

[ * ] Notice: The portion of the term of this patent subsequent to Oct. 8, 2008 has been disclaimed.

[21] Appl. No.: 682,589

[22] Filed: Apr. 8, 1991

Related U.S. Application Data

[63] Continuation of Ser. No. 498,201, Mar. 23, 1990, Pat. No. 5,055,172.

[51] Int. Cl.$^5$ ................................................. C25B 9/00
[52] U.S. Cl. ................................. 204/299 R; 323/250; 323/331; 323/362
[58] Field of Search ................. 204/182.8, 299 R; 323/250, 331, 362

[56] References Cited

U.S. PATENT DOCUMENTS

| | | | |
|---|---|---|---|
| 3,915,827 | 10/1975 | Davies | 204/299 R |
| 4,068,677 | 1/1978 | De Steur et al. | 204/228 |
| 4,327,348 | 4/1982 | Hirayama | 323/250 |
| 4,766,365 | 8/1988 | Bolduc et al. | 323/331 |
| 4,870,327 | 9/1989 | Jorgensen | 315/307 |
| 4,876,638 | 10/1989 | Silva et al. | 323/250 |
| 4,891,103 | 1/1990 | Zorinsky et al. | 204/228 |

OTHER PUBLICATIONS

*Designing With Field-Effect Transistors*, Siliconix, 1981: "Voltage-Controlled Resistors and Fet Current Sources", Chapter 6 (6-1-6-2), pp. 233-242.

Primary Examiner—John Niebling
Assistant Examiner—C. Delacroix-Muirheid
Attorney, Agent, or Firm—D'Alessandro, Frazzini & Ritchie

[57] ABSTRACT

The invention provides an electrophoresis system which separates charged chemical substances by means of applying an electrical potential across a buffer solution which includes those chemical substances. The system of the invention includes a power supply and control system which has a wide dynamic range of constant voltage, current and power which may be supplied, and is therefore particularly suited to the needs of the electrophoresis system. In the invention, the power supply includes a flyback topology and a control system which allows an operator to specify a wide range of constant voltage, current or power supply requirements for the electrophoresis system.

26 Claims, 12 Drawing Sheets

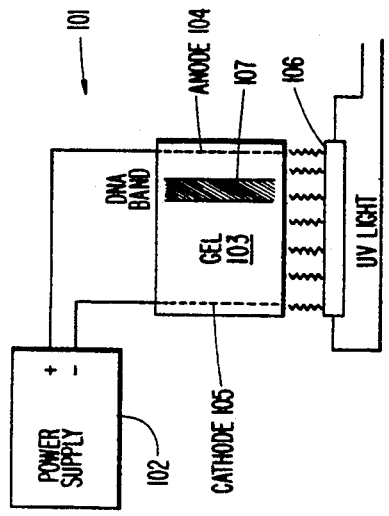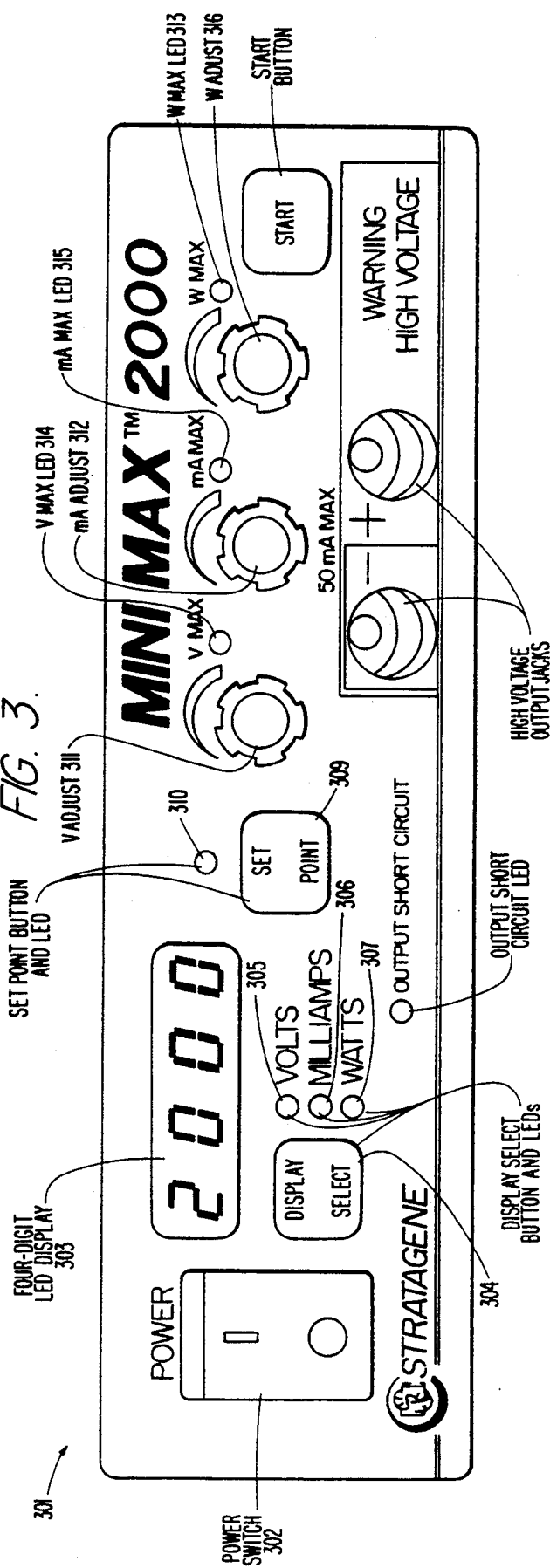

ELECTROPHORESIS SYSTEM

This is a continuation of Ser. No. 07/498,201, filed Mar. 23, 1990, now U.S. Pat. No. 5,055,172 hereby incorporated by reference as if fully set forth herein.

BACKGROUND OF THE INVENTION

1. Field of the Invention

This invention relates to electrophoresis systems. More specifically, this invention relates to an electrophoresis system which makes use of a power supply and control system of particular utility for electrophoresis systems.

2. Description of Related Art

Electrophoresis is a process for separating chemical substances from one another by means of their differential molecular weights. The chemical substances may be naturally charged, or a charge may be applied to them prior to electrophoresis. An electric potential is applied to the mixture for a fixed time period, during which the lighter molecules will move more quickly. At the end of the period, the lighter molecules will have moved farther than the heavier molecules. Thus, one application of this process is to determine relative proportions of chemical substances in a mixture.

One problem which has arisen in the art is the use and control of a power supply which has a sufficient dynamic range for electrophoresis. This problem is particularly acute in electrophoresis of DNA fragments and other bioactive and/or biochemical substances, or in electrophoresis of other chemicals which are to be separated in a gel. The gel commonly has a negative temperature coefficient, so an increase in current causes the gel to heat up and to draw more current. Moreover, a widely varying range of chemicals to be separated, as may be common in electrophoresis of DNA fragments, may require widely varying voltage, current or power requirements.

Prior art electrophoresis systems have attempted to solve this problem by control circuitry for limiting the output of the power supply. However, while this solution will allow the electrophoresis system to operate, it is not as effective or as efficient as if the power supply itself had wide dynamic range, for each of supplied voltage, current and power.

Another problem which has arisen in the art is that prior art power supplies may be large, bulky and very heavy. This causes inconvenience in placing and using the electrophoresis system in a laboratory environment. The circuitry of the present invention offers a size and weight advantage over prior art power supply and control systems.

SUMMARY OF THE INVENTION

The invention provides an electrophoresis system which separates charged chemical substances by means of applying an electrical potential across a buffer solution which includes those chemical substances. The system of the invention includes a power supply and control system which has a wide dynamic range of constant voltage, current and power which may be supplied, and is therefore particularly suited to the needs of the electrophoresis system. In the invention, the power supply includes a flyback topology and a control system which allows an operator to specify a wide range of constant voltage, current or power supply requirements for the electrophoresis system. The circuitry for the power supply and control system is particularly compact and affords a size and weight advantage over prior art systems.

BRIEF DESCRIPTION OF THE DRAWINGS

FIG. 1 is a block diagram of an embodiment of the invention.

FIGS. 3 is a drawing of a set of operator controls in an embodiment of the invention.

DESCRIPTION OF THE PREFERRED EMBODIMENT

Figure 2:
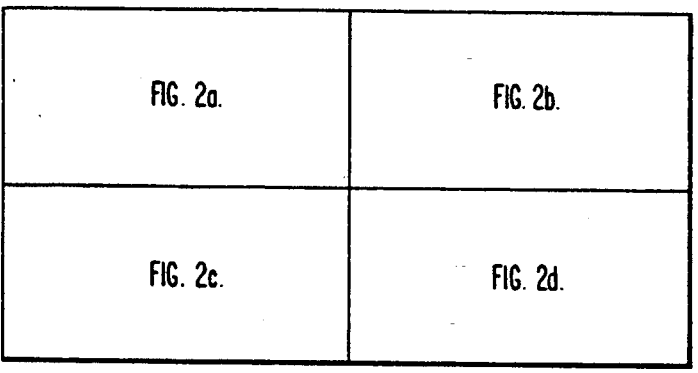
FIG. 2, are a circuit diagram of the power supply and control system element of an embodiment of the invention.

The invention may be used together with several different electrophoresis systems which are not disclosed in detail herein. It would be clear to one of ordinary skill in the art, after perusal of the specification, drawings and claims herein, that coupling of the circuitry disclosed herein to an electrophoresis system of common design would be a straightforward task and would not require undue experimentation. Accordingly, a more detailed description is not included herein.

FIG. 1 is a block diagram of an embodiment of the invention. An electrophoresis system 101 has a power supply and control system 102 which supplies power for the electrophoresis process. In the electrophoresis system 101, a mixture of chemical substances to be separated is embedded in a gel 103 having an anode 104 and a cathode 105 coupled to the power supply and control system 102. In a preferred embodiment, the gel 103 may be soaked in a radioactive probe and an ultraviolet light 106 may be used to illuminate a DNA band 107 which has been separated by the electrophoresis process. A more detailed description of the electrophoresis process and apparatus for conducting the process may be found in "Electrophoresis: Theory, Techniques and Biochemical and Clinical Applications" (2d. ed.), by Anthony T. Andrews, published by Oxford University Press (New York, N.Y.) in 1986, hereby incorporated by reference as if fully set forth herein.

Power Supply and Control System

FIG. 2 is a circuit diagram of the power supply and control system 102 of an embodiment of the invention. The power supply and control system 102 has a main input terminal 201 for accepting AC input power from an external source (not shown) and a main output terminal 202 for generating output power for the electrophoresis system 101. In a preferred embodiment, feedback and operator controls (see FIGS. 3-5) control the operation of the power supply and control system 102.

The main input terminal 201 is coupled to an input 203 of a primary rectifier 204 by means of an EMI filter (not shown). The EMI filter protects the external source from electromagnetic interference which may be generated by the power supply and control system 102, as is well known in the art. In a preferred embodiment, the EMI filter may comprise part number FN 322-6/05 made by Schaffner EMC, Inc. (Union, N.J.). In a preferred embodiment, the primary rectifier 204 may comprise a set of capacitors 205 such as part number LP681M200C4P3 made by Aerovox (Glasgow, Ky.), and a set of diodes 206 such as part number PB66 made by Diodes, Inc. (Chatsworth, Calif.), configured as a full-wave or half-wave bridge rectifier, the structure of which is well known in the art.

An output 207 of the primary rectifier 204 is coupled to a power input 208 of a solid-state switch 209. In a preferred embodiment, the solid-state switch 209 may comprise a pair of 900 volt, 4 amp, MOSFET transistors 210 coupled in parallel, such as part number IXTP4N90 made by IXYS (San Jose, Calif.).

A control input 211 of the solid-state switch 209 is coupled to an output 212 of a main control circuit 213. In a preferred embodiment, the main control circuit 213 may comprise a 55 KHz pulse-width modulator (as set by a timing RC circuit, as is well known in the art) such as part number SG3524B made by Silicon General (Garden Grove, Calif.), arranged in a current mode control configuration, the structure of which is well known in the art, to achieve stability throughout a wide dynamic range. The main control circuit 213 generates a control signal whose duty factor depends upon its own inputs, as disclosed herein.

A power output 214 of the solid-state switch 209 is coupled to an input 215 of a current-sense transformer 216, which generates a signal indicative of current. In a preferred embodiment, the current-sense transformer 216 may comprise part number PE-51688 made by Pulse Engineering (San Diego, Calif.). An output 217 of the current-sense transformer 216 is coupled to a first input 218 of the main control circuit 213 (pin 4 of a preferred part, for primary current limitation).

The power output 214 of the solid-state switch 209 is also coupled to a primary coil 219 of a transformer 220. In a preferred embodiment, the transformer 220 may comprise a high-frequency flyback topology ferrite transformer with the primary coil 219 having 32 turns, a set of four secondary coils 221 each having 65 turns and wound opposite to the primary coil 219, and a total air gap of about 30 thousandths of an inch.

The four secondary coils 221 of the transformer 220 are configured to carry a maximum of about 500 volts each, and are coupled to a set of inputs 222 of a secondary rectifier 223, and the voltages are summed at a set of capacitors 224 of the secondary rectifier 223, such as part number 684MSR630K made by Illinois Capacitor (Lincolnwood, Ill.). In a preferred embodiment, the secondary rectifier 223 may also comprise a set of diodes 225 such as part number MUR180E made by Motorola (Phoenix, Ariz.).

An output 226 of the secondary rectifier 223 is coupled to the main output terminal 202.

Voltage and Current Feedback

The main output terminal 202 also comprises a signal indicating measured voltage, and is coupled to a first input 227 of an error amplifier 228. A second input 229 of the error amplifier 228 accepts a control voltage from a control voltage terminal 230 (see FIG. 4). The error amplifier 228 thus compares the measured voltage with the control voltage. In a preferred embodiment, the error amplifier 228 may comprise an operational amplifier ("op-amp") arranged in an amplifier configuration, the structure of which is well known in the art, such as part number LM358 made by National Semiconductor (Santa Clara, Calif.).

An output 231 of the error amplifier 228 is coupled to an input 232 of a first opto-coupler 233. In a preferred embodiment, the first opto-coupler 233 may comprise a combination of an LED 234 and a phototransistor 235, as is well known in the art, such as part number H11AV2A made by Motorola. An output 236 of the first opto-coupler 233 is coupled to a second input 237 of the main control circuit 213 (pin 5 of a preferred part).

The main output terminal 202 is coupled to the electrophoresis system 101, which imposes an electrical load. As disclosed herein, because the gel 103 commonly has a negative temperature coefficient, an increase in current causes the gel 103 to heat up and causes the electrophoresis system 101 to draw more current.

A current sensor 238 measures a load current of the electrophoresis system 101 and generates a signal indicating measured current. In a preferred embodiment, the current sensor 238 may comprise a set of resistors arranged in series so as to measure current by the voltage drop across the resistors, as is well known in the art.

An i-sense-2 output 239 of the current sensor 238 is coupled to a negative input 240 of a load detection amplifier 241. A positive input 242 of the load detection amplifier 241 is coupled to a 5 mA fixed source 243 indicating 5 mA current. In a preferred embodiment, the load detection amplifier 241 may comprise an op-amp arranged in an amplifier configuration, the structure of which is well known in the art, such as part number LM358 made by National Semiconductor.

The i-sense-2 output 239 is also coupled to a positive input 244 of a short-circuit detection amplifier 245. A negative input 246 of the short-circuit detection amplifier 245 is coupled to a 75 mA fixed source 247 indicating 75 mA current. In a preferred embodiment, the short-circuit detection amplifier 245 may comprise an op-amp 248 arranged in an amplifier configuration, the structure of which is well known in the art, such as part number LM358 made by National Semiconductor, coupled in series with a latch 249 such as part number 74HC74 made by Motorola.

An output 250 of the load detection amplifier 241 is coupled to a wire-OR node 251 by means of a first wire-OR diode 252, and an output 253 of the short-circuit detection amplifier 245 is coupled to the wire-OR node 251 by means of a second wire-OR diode 254. The wire-OR node 251 thus comprises an inhibit signal for the main control circuit 213, and is coupled to an input 255 of a second opto-coupler 256.

In a preferred embodiment, the second opto-coupler 256 may comprise a combination of an LED 257 and a phototransistor 258, as is well known in the art, such as part number H11AV2A made by Motorola. An output 259 of the second opto-coupler 256 is coupled to a third input 260 of the main control circuit 213 (pin 9 of a preferred part, for inhibiting pulse generation).

Front-Panel Operator Controls

FIG. 3 is a drawing of a set of front-panel operator controls 301 in an embodiment of the invention. In a preferred embodiment, the operator controls 301 may comprise the following controls and indicators:

A power switch 302 for turning the power supply on and off, having an "on" position and an "off" position.

A digital display 303. In a preferred embodiment, the digital display 303 may comprise a four-digit LED display, the structure of which is well known in the art.

A display select button 304 for selecting among display based on voltage, current or power, and a set of indicators comprising a voltage indicator 305, a current indicator 306, and a power indicator 307. In a preferred embodiment, these indicators may be visual indicators comprising LED lamps.

An output short-circuit indicator 308. In a preferred embodiment, this indicator may be a visual indicator comprising an LED lamp.

A set-point button 309 for selecting and deselecting a set-point, and a set-point indicator 310 for indicating when a set-point is selected. In a preferred embodiment, the set-point indicator 310 may be a visual indicator comprising an LED lamp.

A set of adjustment controls comprising a voltage control 311, a current control 312 and a power control 313, for adjusting the desired voltage, current, and power respectively, each having a maximum-value indicator for voltage maximum 314, current maximum 315 or power maximum 316 respectively, for indicating when a maximum value has been selected. In a preferred embodiment, these maximum-value indicators may each be a visual indicator comprising an LED lamp.

A start button 317 for starting the power supply.

Effect of Feedback Controls

Figure 4:
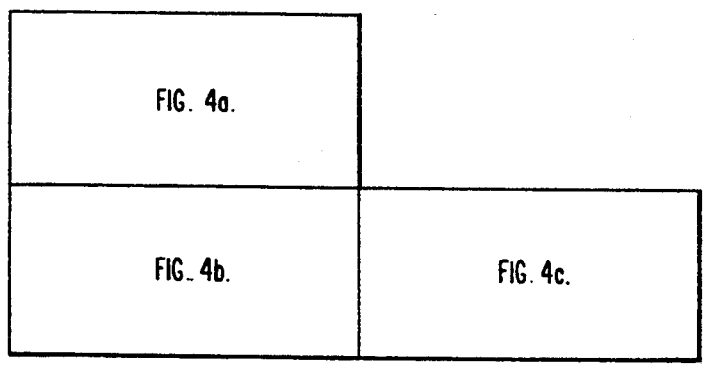
FIG. 4, are a circuit diagram of a feedback control section of an embodiment of the invention.

FIG. 4 is a circuit diagram of a feedback control section of an embodiment of the invention.

The operator controls 301 are coupled to a current control output 401, a voltage control output 402 and a power control output 403.

The current control output 401 is coupled to a first input 404 of a current differential amplifier 405. A second input 406 of the current differential amplifier 405 is coupled to the i-sense-2 output 239 of the current sensor 238.

The current differential amplifier 405 compares the load current of the electrophoresis system 101 with the desired current set by the operator by means of the current control 312. In a preferred embodiment, the current differential amplifier 405 may comprise a set of two op-amps 407 and 408 arranged in an amplifier configuration for positive swing only, the structure of which is well known in the art, such as part numbers LM301A and LM358 respectively, made by National Semiconductor.

An output 409 of the current differential amplifier 405 is coupled to an input 410 of a current nonlinear amplifier 411. The current nonlinear amplifier 411 comprises an amplifier op-amp 412 coupled in an amplifier feedback configuration with an amplifier transistor 413 coupled between a negative input 414 and an output 415 of the amplifier op-amp 412. In a preferred embodiment, the amplifier op-amp 412 may comprise part number LM358 made by National Semiconductor and the amplifier transistor 413 may comprise part number 2N4220 made by Motorola.

An output 416 of the current nonlinear amplifier 411 is coupled to a first summing input 417 of a summing amplifier 418.

The voltage control output 402 is coupled to a second summing input 419 of the summing amplifier 418.

The power control output 403 is coupled to a first input 420 of a power differential amplifier 421. A second input 422 of the power differential amplifier 421 is coupled to a calculated power output 423 of the multiplier 502 (see FIG. 2) which calculates a product of measured current and measured voltage.

The power differential amplifier 421 compares the measured power of the electrophoresis system 101 with the desired power set by the operator by means of the power control 313. In a preferred embodiment, the power differential amplifier 421 may comprise a set of two op-amps 424 and 425 arranged in an amplifier configuration for positive swing only, in like manner as the current differential amplifier 405, such as part numbers LM301A and LM358 respectively, made by National Semiconductor.

An output 426 of the power differential amplifier 421 is coupled to an input 427 of a power nonlinear amplifier 428. In a preferred embodiment, the power nonlinear amplifier 428 comprises an op-amp 429 and a transistor 430 configured in like manner as the current nonlinear amplifier 411.

An output 431 of the power nonlinear amplifier 428 is coupled to a third summing input 432 of the summing amplifier 418.

In a preferred embodiment, the summing amplifier 418 may comprise a summing node 433 which is coupled to the first summing input 417, the second summing input 419 and the third summing input 432. The summing node 433 is coupled to an input 434 of an op-amp 435 configured in an amplifier configuration, the structure of which is well known in the art, such as part number LM358 made by National Semiconductor.

An output 436 of the summing amplifier 418 is coupled to an input 437 of an invertor 438. In a preferred embodiment, the invertor 438 may comprise an op-amp configured in an inverting configuration, the structure of which is well known in the art, such as part number LM358 made by National Semiconductor.

An output 439 of the invertor 438 is coupled to the control voltage terminal 230.

Effect of Display Controls

Figure 5:
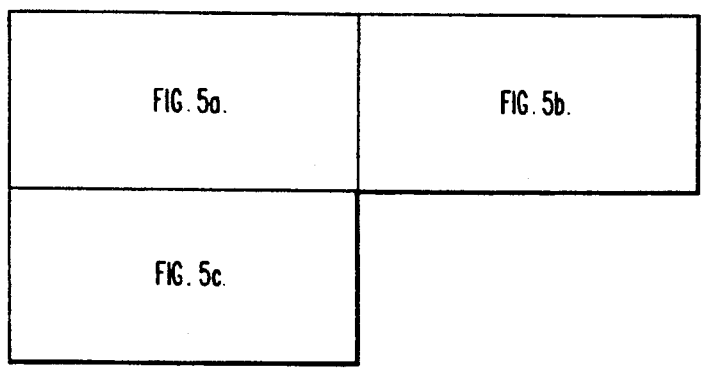
FIGS. 5A-5C, collectively FIG. 5, a circuit diagram of a display control section of an embodiment of the invention.
Figure 2A:
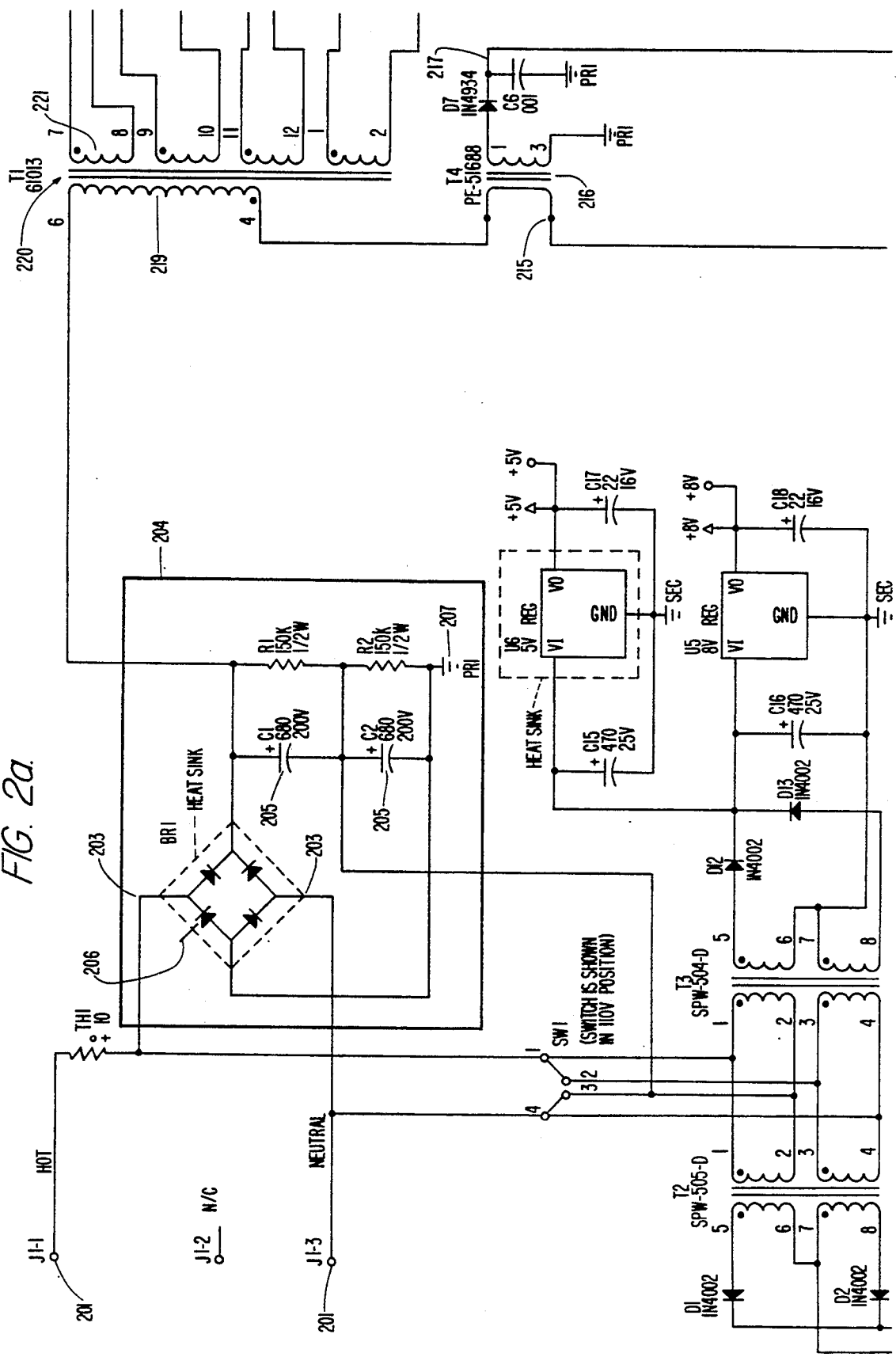
FIG. 2A-2D, collectively
Figure 2B:
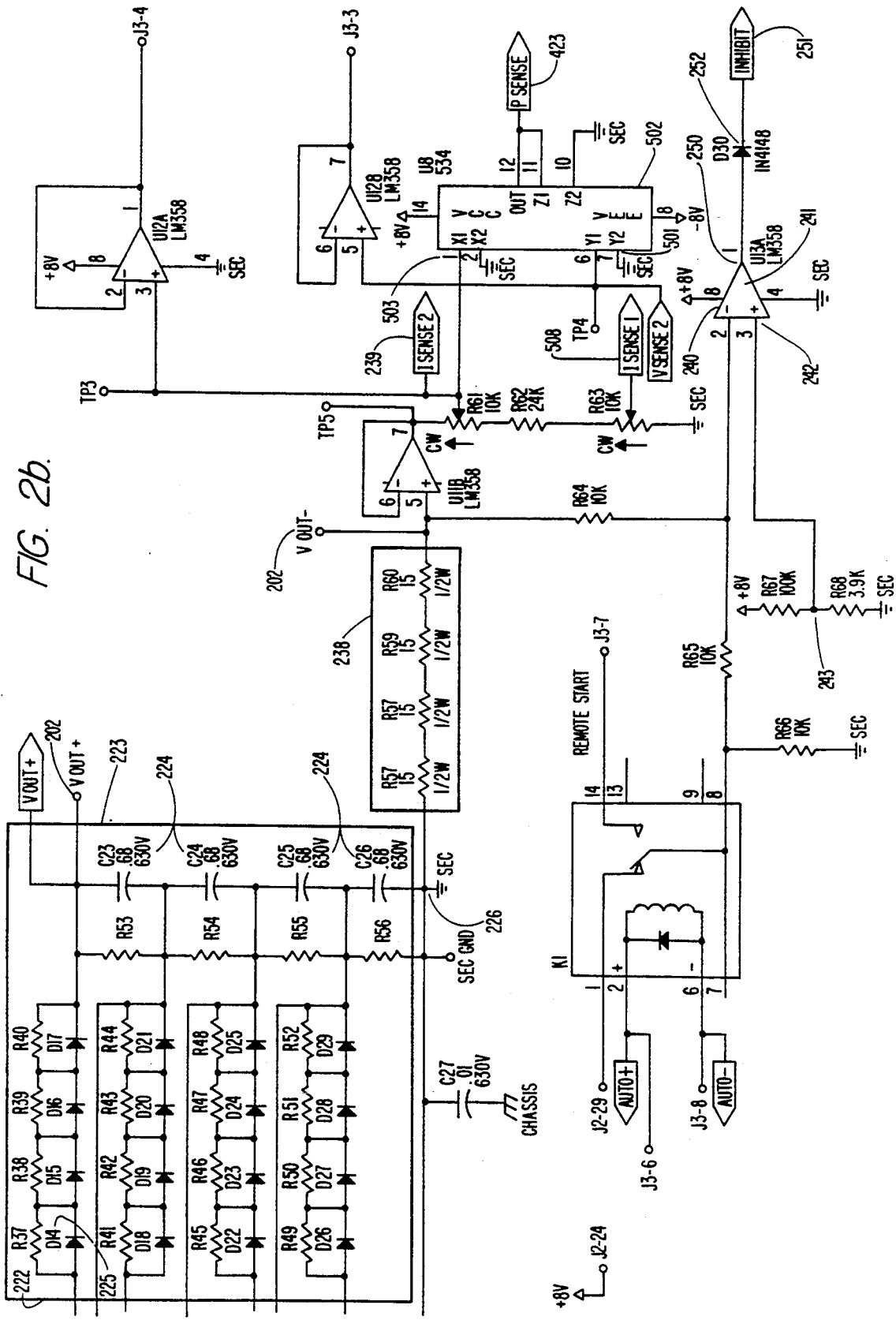
Figure 2C:
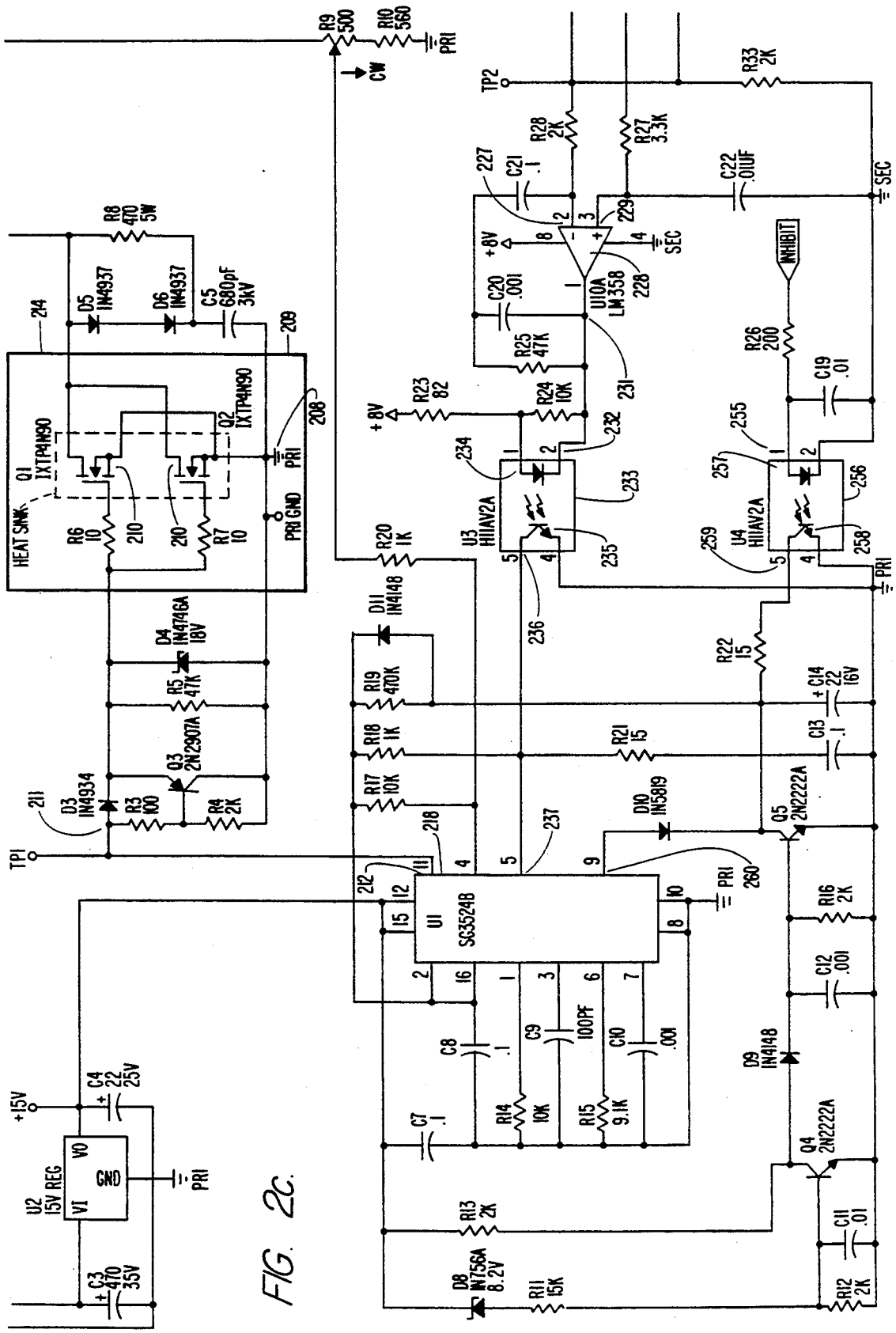
Figure 2D:
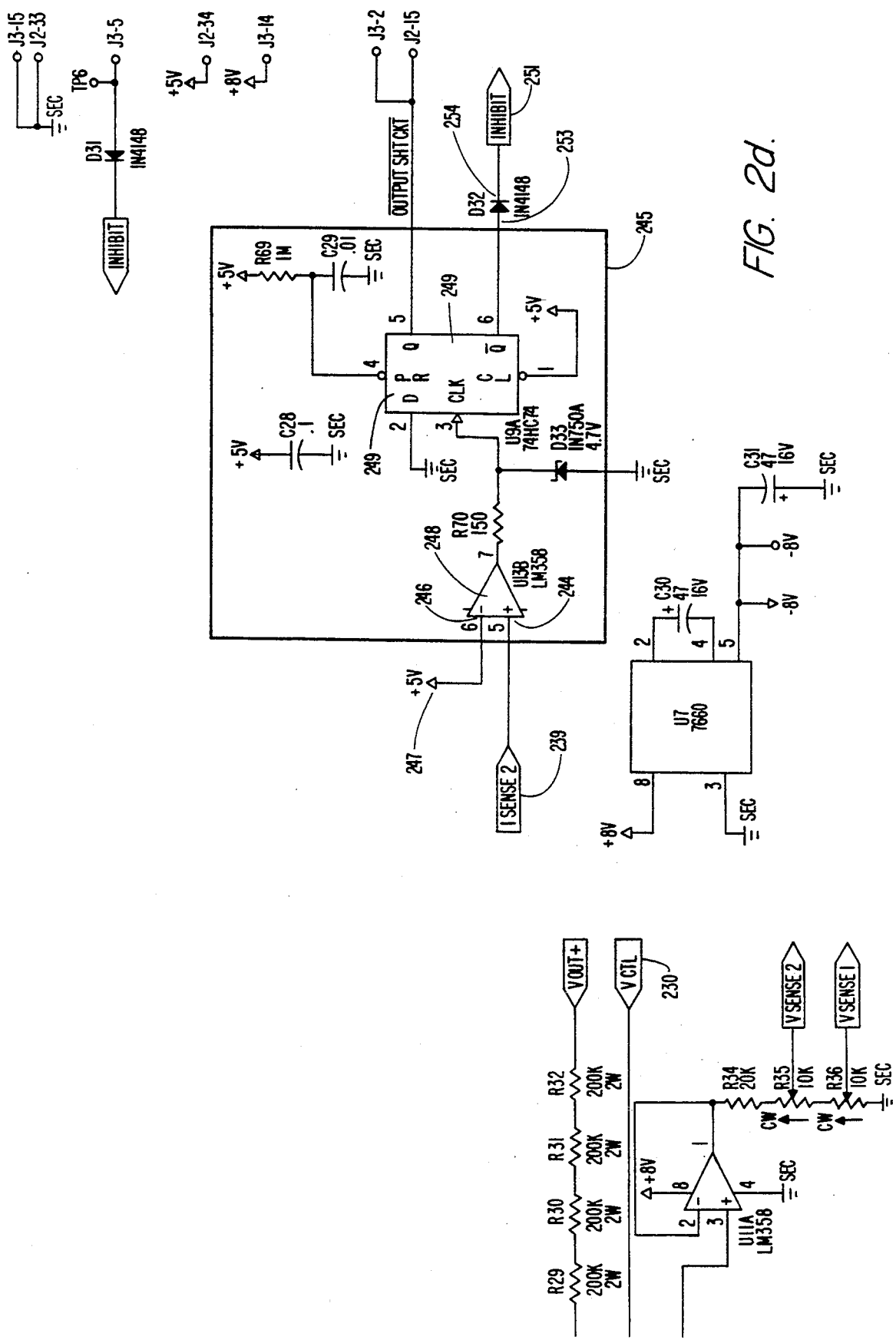
Figure 4A:
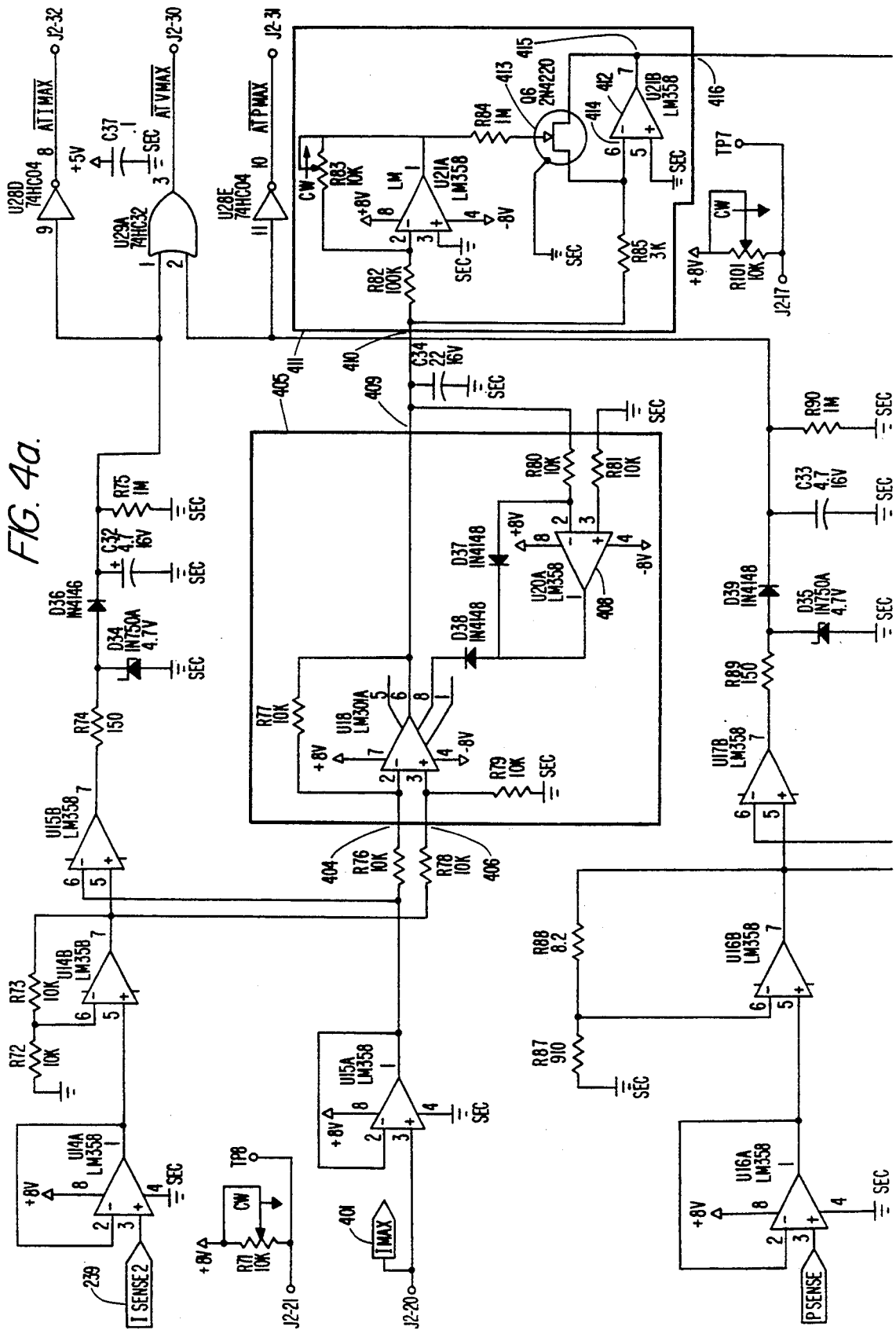
FIGS. 4A-4C, collectively
Figure 4B:
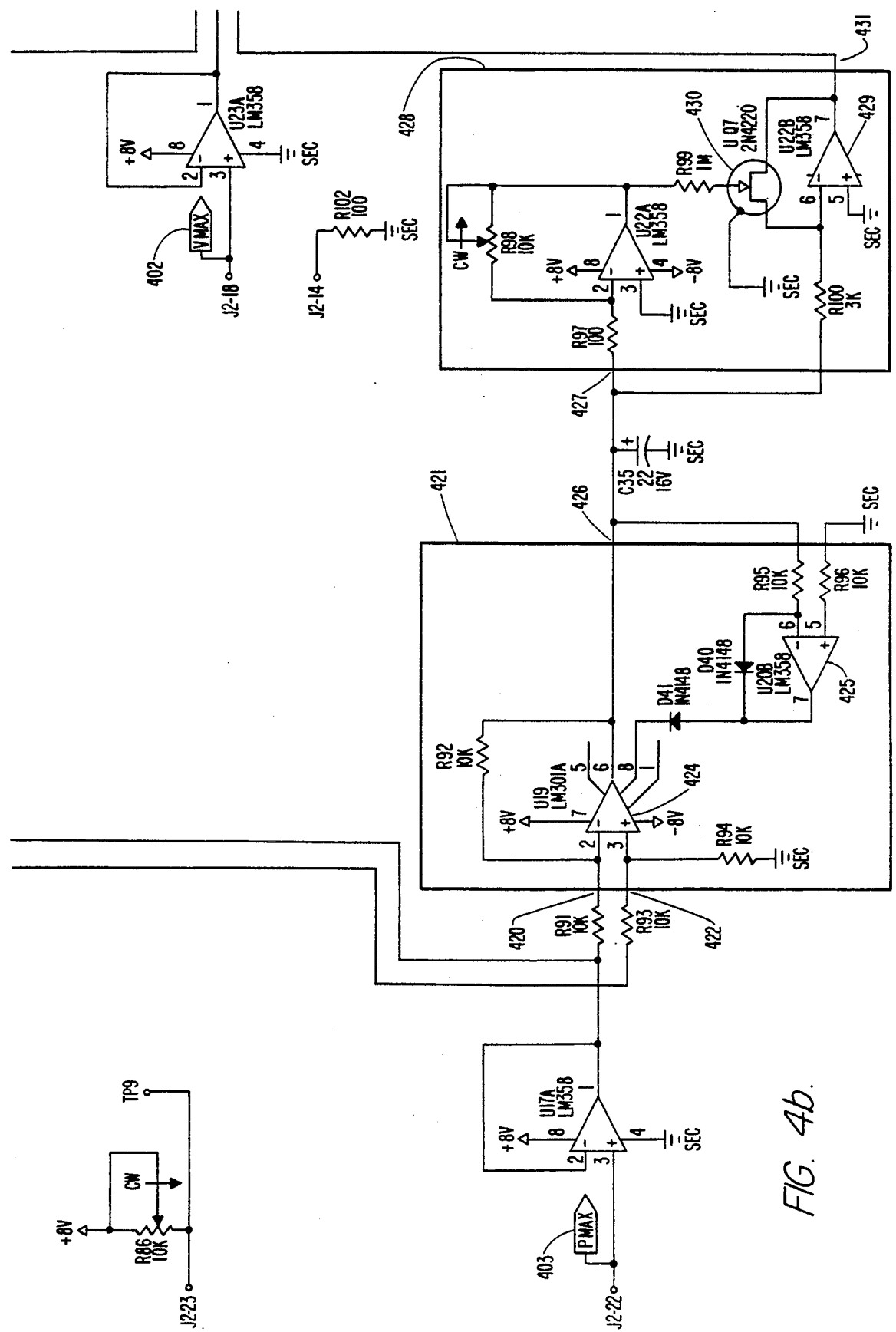
Figure 4C:
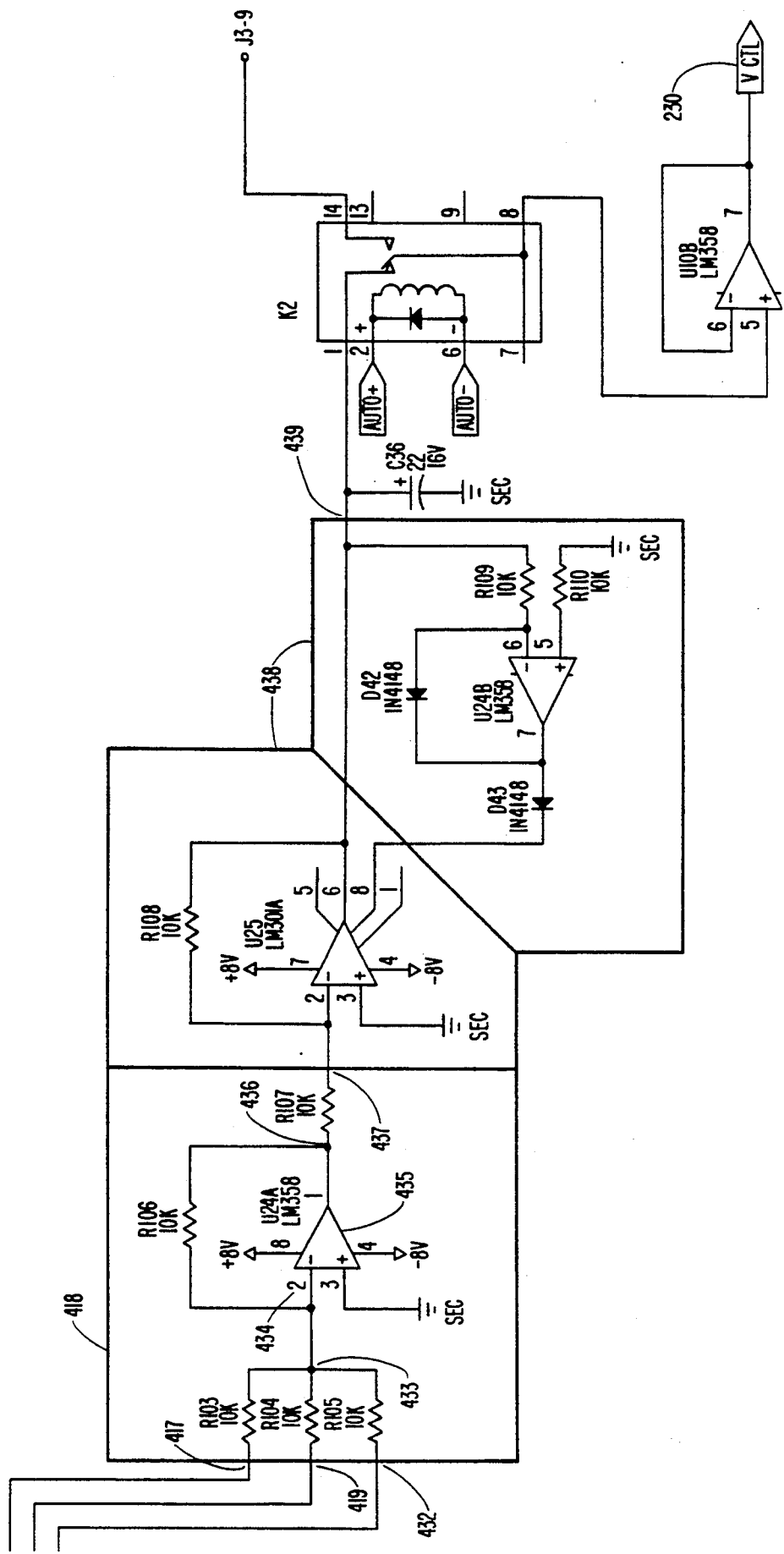
Figure 5A:
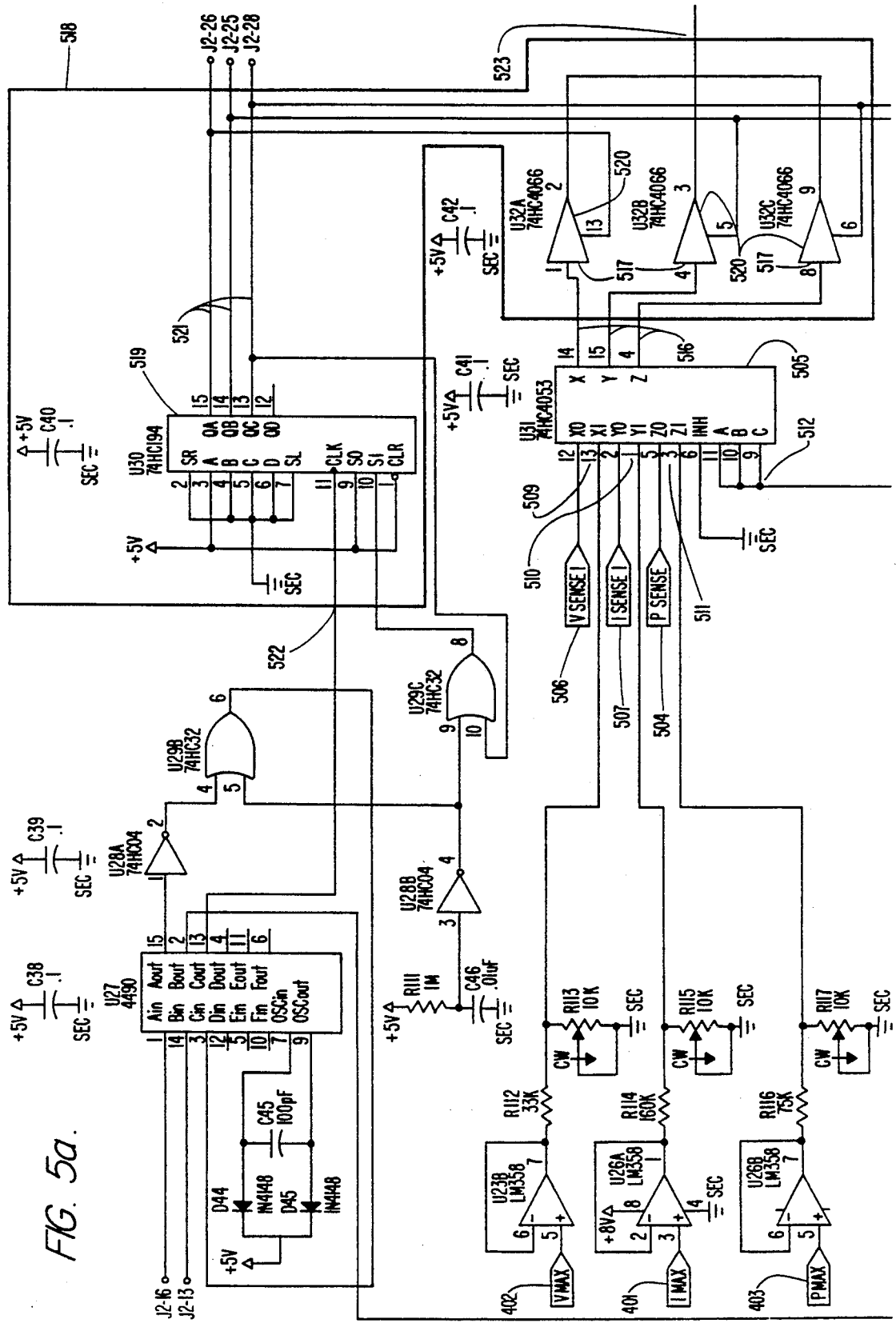
Figure 5B:
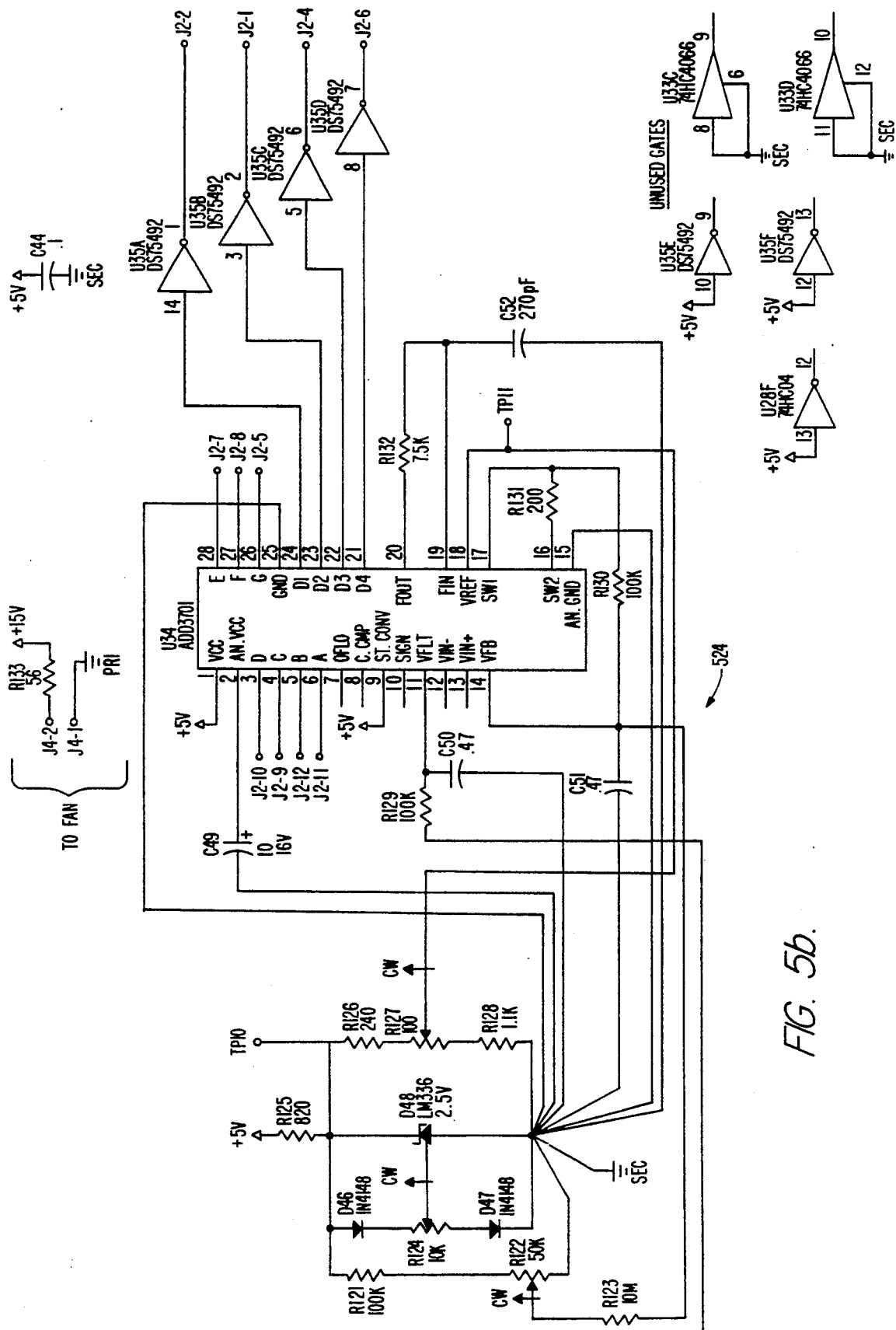
Figure 5C:
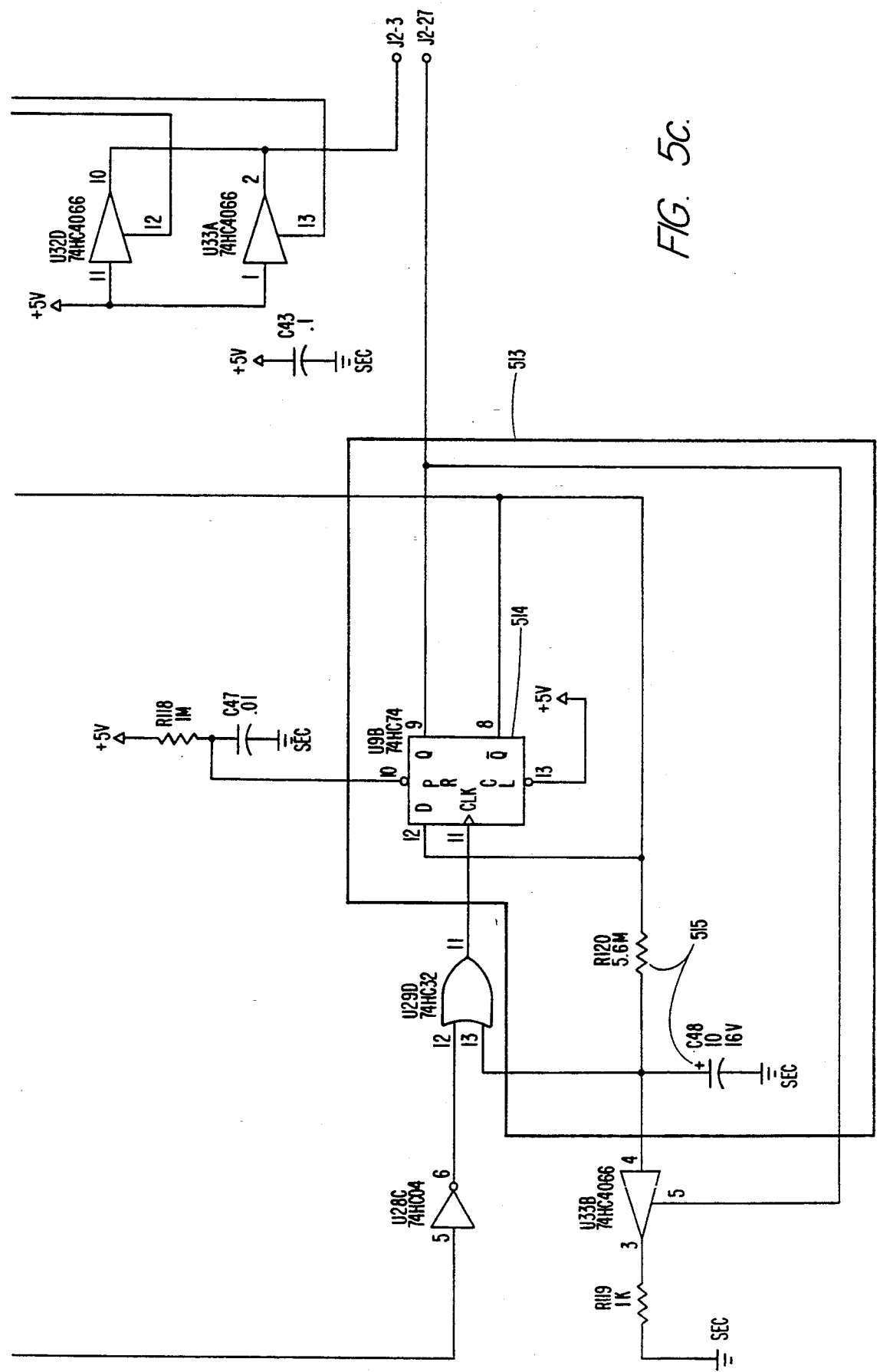

FIG. 5 is a circuit diagram of a display control section of an embodiment of the invention.

A voltage input 501 of a multiplier 502 (see FIG. 2) is coupled to the main output terminal 202, indicating measured voltage. A current input 503 of the multiplier 502 is coupled to the i-sense-2 output 239, indicating measured current. In a preferred embodiment, the multiplier 502 may comprise an analog multiplier such as part number AD534JD made by Analog Devices (Norwood, Mass.).

The calculated power output 423 of the multiplier 502 is coupled to a first power input 504 of a normal/set switch 505, indicating measured power. A first voltage input 506 of the normal/set switch 505 is coupled to the main output terminal 202, indicating measured voltage. A first current input 507 of the normal/set switch 505 is coupled to an i-sense-1 output 508 of the current sensor 238, indicating measured current. In a preferred embodiment, the i-sense-1 output 508 and the i-sense-2 output 239 differ because they have differing voltage levels for the same indicated current.

The voltage control output 402 is coupled to a second voltage input 509 of the normal/set switch 505. The current control output 401 is coupled to a second current input 510 of the normal/set switch 505. The power control output 403 is coupled to a second power input 511 of the normal/set switch 505.

The set-point button 309 is coupled to a control input 512 of the normal/set switch 505 by means of a one-shot logic element 513, comprising a set-point latch 514 and a timeout element 515 configured to set the set-point latch 514 when the set-point button 309 is pressed and to reset the set-point latch 514 after a fixed period of time, as would be clear to those of ordinary skill in the art. The normal/set switch 505 selects between its first and second voltage, current and power inputs respectively. In a preferred embodiment, the normal/set switch 505 may comprise a multiplexor such as part number 74HC4053 made by Motorola.

A set of three outputs 516 of the normal/set switch 505, for voltage, current and power respectively, are coupled to a set of three inputs 517 respectively of a display select mux 518. The display select mux 518 selects among its voltage, current and power inputs. In a preferred embodiment, the display select mux 518 may comprise a shift register 519, such as part number 74HC194 made by Motorola, for indicating which one of voltage, current or power is selected, and a set of three analog switches 520, such as part number 74HC4066 made by Motorola, each of which is controlled by an output 521 of the shift register 519. The display select button 304 is coupled to a control input 522 of the shift register 519.

An output 523 of the display select mux 518 is coupled to the digital display 303 by means of a display driver 524. In a preferred embodiment, the display driver 524 may comprise an A/D converter and a display driver combined in one circuit, the structure of which is well known in the art, such as part number ADD3701CCN made by National Semiconductor.

The circuitry for the power supply and control system 102 which has been described above is particularly compact and affords a size and weight advantage over prior art systems.

While preferred embodiments are disclosed herein, many variations are possible which remain within the concept and scope of the invention, and these variations would become clear to one of ordinary skill in the art after perusal of the specification, drawings and claims herein.

We claim:

1. An electrophoresis system for separating charged chemical substances, comprising
   means for applying an electrical potential to a mixture of said charged chemical substances;
   first means for generating a first control signal indicating an electrical supply parameter;
   second means for generating a second control signal indicating a choice of level of supply;
   third means for generating a constant level of supply of said electrical potential as indicated by said first control signal and second control signal, comprising a flyback transformer having a characteristic frequency exceeding about 20 kilohertz and having at least one primary winding and at least one secondary winding with opposite polarity and having a ferrite core with an air gap.

2. An electrophoresis system as in claim 1, wherein said electrical supply parameter is voltage, current, or power.

3. An electrophoresis system as in claim 1, wherein said third means for generating weighs less than about 6 pounds.

4. An electrophoresis system as in claim 1, wherein said transformer comprises a plurality of secondary windings having opposite polarity from said primary winding and coupled to diode rectifiers, said diode rectifiers being coupled in series.

5. An electrophoresis system as in claim 1, wherein said third means for generating comprises
   a switch coupled to said transformer and coupled to an input power source;
   a circuit coupled to a control input of said switch and providing a control signal, whereby said switch causes said power source and said transformer to be coupled in accordance with said control signal; and
   a feedback circuit coupling an output of said third means for generating to said circuit.

6. An electrophoresis system as in claim 5, wherein said feedback circuit comprises at least one second circuit coupled to a signal indicating a desired supplied electrical level and to a signal indicating a sensed supplied electrical level, said second circuit comprising a transistor coupled between an input and an output of an amplifier.

7. An electrophoresis system as in claim 6, comprising a plurality of said second circuits coupled to a summing circuit.

8. A system comprising
   means for applying an electrical potential;
   first means for generating a first control signal indicating constant voltage, constant current, or constant power supply;
   second means for generating a second control signal indicating a choice of level of supply;
   third means for generating a constant level of supply of said electrical potential as indicated by said first control signal and second control signal, comprising a flyback transformer having a characteristic frequency exceeding about 20 kilohertz and having at least one primary winding and at least one secondary winding with opposite polarity and having a ferrite core with an air gap.

9. A system as in claim 8, wherein said third means for generating weighs less than about 6 pounds.

10. A system as in claim 8, wherein said transformer comprises a plurality of secondary windings having opposite polarity from said primary winding and coupled to diode rectifiers, said diode rectifiers being coupled in series.

11. A system as in claim 8, wherein said third means for generating comprises
    a switch coupled to said transformer and coupled to an input power source;
    a circuit coupled to a control input of said switch and providing a control signal, whereby said switch causes said power source and said transformer to be coupled in accordance with said control signal; and
    a feedback circuit coupling an output of said third means for generating to said circuit.

12. A system as in claim 11, wherein said circuit is arranged in a current mode control configuration.

13. A system as in claim 11, wherein said feedback circuit comprises at least one second circuit coupled to a signal indicating a desired supplied electrical level and to a signal indicating a sensed supplied electrical level, said second circuit comprising a transistor coupled between an input and an output of an amplifier.

14. A system as in claim 13, wherein said supplied electrical level is voltage, current, or power.

15. A system as in claim 13, comprising a plurality of said second circuits coupled to a summing circuit.

16. Apparatus for generating a constant level of electrical supply, comprising a flyback transformer having a characteristic frequency exceeding about 20 kilohertz, having at least one primary winding, having a ferrite core with an air gap, and having a plurality of secondary windings having opposite polarity from said primary winding and coupled to a summing circuit.

17. Apparatus as in claim 16, wherein said summing circuit is a voltage summing circuit or a current summing circuit.

18. Apparatus as in claim 16, wherein at least one of said secondary windings is coupled to a diode rectifier.

19. Apparatus as in claim 16, wherein a plurality of said secondary windings are each coupled to a diode rectifier, and said diode rectifiers being coupled in series.

20. Apparatus as in claim 16, comprising
a switch coupled to said transformer and coupled to an input power source;
a circuit coupled to a control input of said switch and providing a control signal, whereby said switch causes said power source and said transformer to be coupled in accordance with said control signal; and
a feedback circuit coupling at least one of said plurality of secondary windings to said circuit.

21. Apparatus as in claim 20, wherein said feedback circuit comprises at least one second circuit coupled to a signal indicating a desired supplied electrical level and to a signal indicating a sensed supplied electrical level, said second circuit comprising a transistor coupled between an input and an output of an amplifier.

22. Apparatus as in claim 21, comprising a plurality of said second circuits coupled to a summing circuit.

23. Apparatus for generating a constant level of electrical supply, comprising
a flyback transformer having a characteristic frequency exceeding about 20 kilohertz and having at least one primary winding and at least one secondary winding with opposite polarity and having a ferrite core with an air gap;
a switch coupled to said transformer and coupled to an input power source;
a circuit coupled to a control input of said switch and providing a control signal, whereby said switch causes said power source and said transformer to be coupled in accordance with said control signal; and
a feedback circuit coupling at least one of said plurality of secondary windings to said circuit, said feedback circuit comprising at least one second circuit coupled to a signal indicating a desired supplied electrical level and to a signal indicating a sensed supplied electrical level, said second circuit comprising a transistor coupled between an input and an output of an amplifier.

24. Apparatus for generating a constant level of electrical supply, comprising
a flyback transformer having a characteristic frequency exceeding about 20 kilohertz and having at least one primary winding and at least one secondary winding with opposite polarity and having a ferrite core with an air gap;
a switch coupled to said transformer and coupled to an input power source;
a circuit coupled to a control input of said switch and providing a control signal, whereby said switch causes said power source and said transformer to be coupled in accordance with said control signal; and
a feedback circuit coupling at least one of said plurality of secondary windings to said circuit, said feedback circuit comprising at least one second circuit coupled to a signal indicating a desired supplied electrical level and to a signal indicating a sensed supplied electrical level, said second circuit comprising a plurality of amplifiers each coupled to a summing circuit.

25. Apparatus as in claim 24, wherein at least one of said amplifiers has nonlinear gain.

26. Apparatus as in claim 24, wherein at least one of said amplifiers comprises a transistor coupled between an input and an output of an amplifier.

* * * * *